United States Patent
Heyman

[11] Patent Number: 5,954,652
[45] Date of Patent: Sep. 21, 1999

[54] SLIPOVER ILLUMINATING URETERAL CATHETER AND METHOD OF INSTALLATION

[75] Inventor: Arnold M. Heyman, Los Angeles, Calif.

[73] Assignee: Cogent Light Technologies, Inc., Santa Clarita, Calif.

[21] Appl. No.: 08/489,766

[22] Filed: Jun. 13, 1995

[51] Int. Cl.[6] .................................................. A61B 6/00
[52] U.S. Cl. ............................ 600/435; 600/249; 600/585
[58] Field of Search ........................... 128/664, 665; 600/126, 135, 5, 433, 249; 606/32, 34, 41, 170, 167

[56] References Cited

U.S. PATENT DOCUMENTS

| | | | |
|---|---|---|---|
| 3,886,933 | 6/1975 | Mori et al. ................................ | 128/7 |
| 4,198,960 | 4/1980 | Utsugi ....................................... | 128/6 |
| 4,248,214 | 2/1981 | Hannah et al. . | |
| 4,567,882 | 2/1986 | Heller ....................................... | 600/249 |
| 4,757,431 | 7/1988 | Cross et al. .............................. | 362/261 |
| 5,042,915 | 8/1991 | Akutso et al. ............................ | 359/230 |
| 5,159,920 | 11/1992 | Conoon et al. ........................... | 600/129 |
| 5,188,596 | 2/1993 | Condon et al. ........................... | 604/101 |
| 5,250,025 | 10/1993 | Sosnowski et al. ...................... | 604/51 |
| 5,263,962 | 11/1993 | Johnson et al. .......................... | 606/192 |
| 5,320,639 | 6/1994 | Rudnick ................................... | 606/213 |
| 5,326,751 | 7/1994 | Demopoulos ............................ | 514/167 |
| 5,401,257 | 3/1995 | Chevalier, Jr. et al. ................. | 604/265 |
| 5,423,321 | 6/1995 | Fontenot .................................. | 128/664 |
| 5,439,000 | 8/1995 | Gunersch et al. ........................ | 128/664 |
| 5,441,497 | 8/1995 | Narciso, Jr. .............................. | 606/15 |
| 5,517,997 | 5/1996 | Fontenot .................................. | 600/473 |
| 5,531,741 | 7/1996 | Barbacci ................................... | 606/15 |
| 5,531,751 | 7/1996 | Barbacci ................................... | 606/15 |

FOREIGN PATENT DOCUMENTS

| | | |
|---|---|---|
| 0411265 | 5/1990 | European Pat. Off. . |
| 9400051 | 1/1994 | WIPO . |

*Primary Examiner*—Cary O'Connor
*Assistant Examiner*—Pamela L. Wingood
*Attorney, Agent, or Firm*—Rothwell, Figg, Ernst & Kurz, p.c.

[57] ABSTRACT

A ureteral catheter device composed of a catheter made of light transmitting material, the catheter having a distal end and a proximal end, and being formed to have a drainage lumen that extends between, and is open at the distal and proximal ends, and a second lumen that extends substantially parallel to the drainage lumen; and a single fiber optic filament housed in the second lumen, the fiber optic filament being provided to conduct light in a manner to illuminate the catheter.

25 Claims, 2 Drawing Sheets

SLIPOVER ILLUMINATING URETERAL CATHETER AND METHOD OF INSTALLATION

BACKGROUND OF THE INVENTION

The present invention relates to devices for use in surgical procedures which are performed in proximity to one or both ureters of a patient, and in which it is necessary for the operating physician to be aware of the location of the ureter or ureters in order to assure that they will not be injured by the surgical procedure.

In various operations involving inflammatory or malignant tumors in the pelvis or abdomen, as well as other explorations and procedures, it may be difficult for the operating physician to be aware of the location of the ureters. By way of example, in laparoscopic abdominal and pelvic surgery, the operating physician may have limited vision of the surgical site and also does not have benefit of tactile input which is available during conventional open surgery. Therefore, there is an increased risk of injury to the ureter during such surgery.

It has already been proposed in the art to reduce the risk of ureteral injury by introducing a light source into one or each ureter. Light from the source will diffuse through the ureter wall, thus making the ureter visible to the operating surgeon.

Two devices of this type have been proposed. One of these, marketed by Pilling Rusch (a International Company), utilizes a Bush Ureteral Illuminator in association with a transparent ureteral catheter. The Illuminator includes two fiber-optic bundles with light-emitting segments along its ureteral length. Each of these bundles can be introduced into a transparent ureteral catheter after each catheter has been inserted into a respective ureter. When the Illuminator is connected to a light source, the ureters may be illuminated for visualization.

Another illuminator, a fiber optic ureteral probe, is marketed by Karl Storz. This device is an illuminating ureteral probe designed for illuminating the ureter during operative procedures. The device consists of cold light fibers constructed to create a band of light every centimeter along its length, to aid in measurement. The probe is connected to a cold light fountain and is placed in the ureter by a cystoscope before or in the course of a surgical procedure. The probe can be both palpated and, as a result of the light emission, visualized during a surgical procedure.

Both of the above-described devices have several drawbacks, including the fact that they are difficult to insert in a ureter, particularly when there is secondary pathology in the pelvis or a stenosis in the ureter. As a result, on many occasions, the illuminating device would not be properly placed. In addition, assembly of the known Bush device requires insertion of the optical fiber bundles into the catheters in the operating theater after cystoscopic placement of the catheters, which is a difficult exercise. The device does not have an effective system for securing the fiber bundles in the catheters, and many times they will migrate out of the catheters.

Furthermore, the known devices essentially completely fill the ureteral channel, preventing proper drainage of urine during the time the devices are in place.

SUMMARY OF THE INVENTION

It is an object of the present invention to overcome the above-mentioned drawbacks and difficulties.

A specific object of the invention is to provide a ureteral illuminating device which is ready for use in the operating theater.

Another object of the invention is to provide a ureteral illuminating device which is easily inserted, by passage over a guide wire, up into a ureter and up into the kidney.

Another object of the invention is to provide a ureteral illuminating device which permits drainage of urine from the associated kidney when the device is installed in a ureter.

A further object of the invention is to provide a ureteral illuminating device which can be manufactured at low cost, and can thus be made disposable.

A further object of the invention is to facilitate insertion of a ureteral stent into a ureter after a surgical procedure.

An additional object of the invention is to provide a conduit for injection of color or radiographic dye.

The above and other objects are achieved, according to the invention, by the provision of a ureteral catheter device comprising a catheter made of light transmitting material and being formed to have a drainage lumen that extends between its distal and proximal ends and is open at both ends, and a second lumen that extends substantially parallel to the drainage lumen; and a single light transmitting fiber housed in the second lumen, the fiber being provided to conduct light in a manner to illuminate the catheter.

Furthermore, the novel device according to the invention can be inserted according to an improved method which includes introducing a guide wire into the ureter at cystoscopy via the patient's bladder, and placing the catheter so that it passes over the guide wire and advancing the catheter over the guide wire and into the ureter and up into the kidney.

Thus, a device according to the invention consists essentially of a ureteral catheter made of transparent or translucent material and provided with two lumens; a drainage lumen, which also serves as a guide wire lumen, and a fiber optic receiving lumen containing a single fiber. While the first-mentioned lumen extends throughout the entire length of the catheter, and is open at both ends thereof, the fiber optic receiving lumen is preferably sealed at the distal end of the catheter. The fiber optic will be coupled to an outside light source via a connector.

Because the catheter is provided with a lumen which can serve as a guide wire lumen, insertion of the catheter into a ureter is greatly simplified. In addition, the lumen containing the guide wire will also serve as a urine drainage lumen, which can be given a larger drainage cross section by removal of the guide wire. The drainage lumen can also be used to inject radiographic or colored dye.

After a procedure, the drainage lumen can be used for reinsertion of a guide wire. Then, the ureteral catheter can be withdrawn from the ureter and the guide wire can be left in place. Subsequently, the guide wire can be used for the insertion of a ureteral stent, such as, for example, a double J stent, into the ureter and kidney for drainage and protection of the upper urinary tract.

DESCRIPTION OF THE PREFERRED EMBODIMENTS

Figure 1:
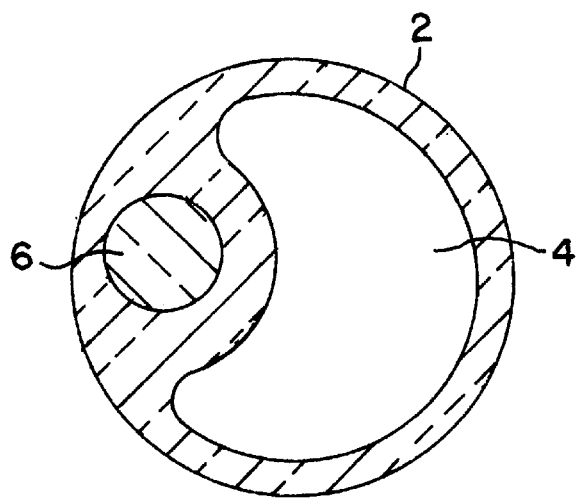
FIG. 1 is a cross-sectional view of a preferred embodiment of a catheter device according to the invention.

As is apparent from the cross-sectional view shown in FIG. 1, a catheter device according to the invention can have a relatively simple structure, which helps to maintain a low manufacturing cost. The catheter device can be made of a reusable material or can be disposable.

The catheter device is composed essentially of an extruded body 2 of plastic material, constituting the catheter proper. Body 2 can be made of any plastic material having mechanical and biological properties suitable for insertion into a body passage of a surgical patient and having a suitable degree of transparency or translucency for conducting light. Body 2 is formed to contain a first lumen 4 which extends along essentially the entire length of the catheter device and opens at both ends thereof.

Body 2 is provided with a further lumen which receives a fiber optic filament 6.

Figure 2:
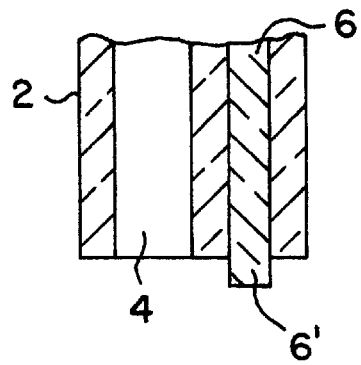
FIG. 2 is a cross-sectional detail view of the proximal end of the catheter of FIG. 1.

FIG. 2 shows the proximal end of the catheter device and shows that the proximal end of filament 6 has a light input end 6' which is constructed to be coupled to a light source in a manner to achieve a high light transmission efficiency. An exemplary light source that may be used is disclosed in U.S. Pat. No. 4,757,431, issued to Cross et al. on Jul. 12, 1980.

FIG. 2 further shows that, in the preferred embodiment, lumen 4 also extends to, and opens at, the proximal end 8 of body 2.

The device shown in FIGS. 1 and 2 may be manufactured by simply extruding body 2 around filament 6. Alternatively, the lumen for receiving filament 6 can be made large enough to permit the filament to be inserted therein after manufacture of body 2.

The device according to the invention is constructed to cause light which is introduced into filament 6 via input end 6' to be emitted laterally from filament 6 into body 2 and to then be emitted laterally from the outer peripheral wall of body 2. Preferably, light is emitted around the entire circumference of body 2 and is emitted as uniformly as possible around the circumference.

Light which has been introduced into filament 6 via input end 6' can be caused to be transmitted and emitted in the above-described manner by any suitable known technique. For example, the periphery of filament 6 can be abraded to promote emission of light laterally into body 2 along a substantial portion of the length of body 2.

The diameter of body 2 may be of the order of 6 French, and lumen 4 is preferably made as large as possible, taking into account the necessary diameter of filament 6 and the necessary wall thickness of body 2.

According to a presently preferred practical embodiment of the invention, lumen 4 is given a diameter sufficient to receive a guide wire having a diameter of 0.038 inch, filament 6 has a diameter of 470 microns and body 2 has a standard ureteral catheter length of 70 centimeters. As is known in this art, body 2 may be provided with markings at intervals of every 5 centimeters from the distal end, with a total of 10 such markings being provided.

Figure 3:
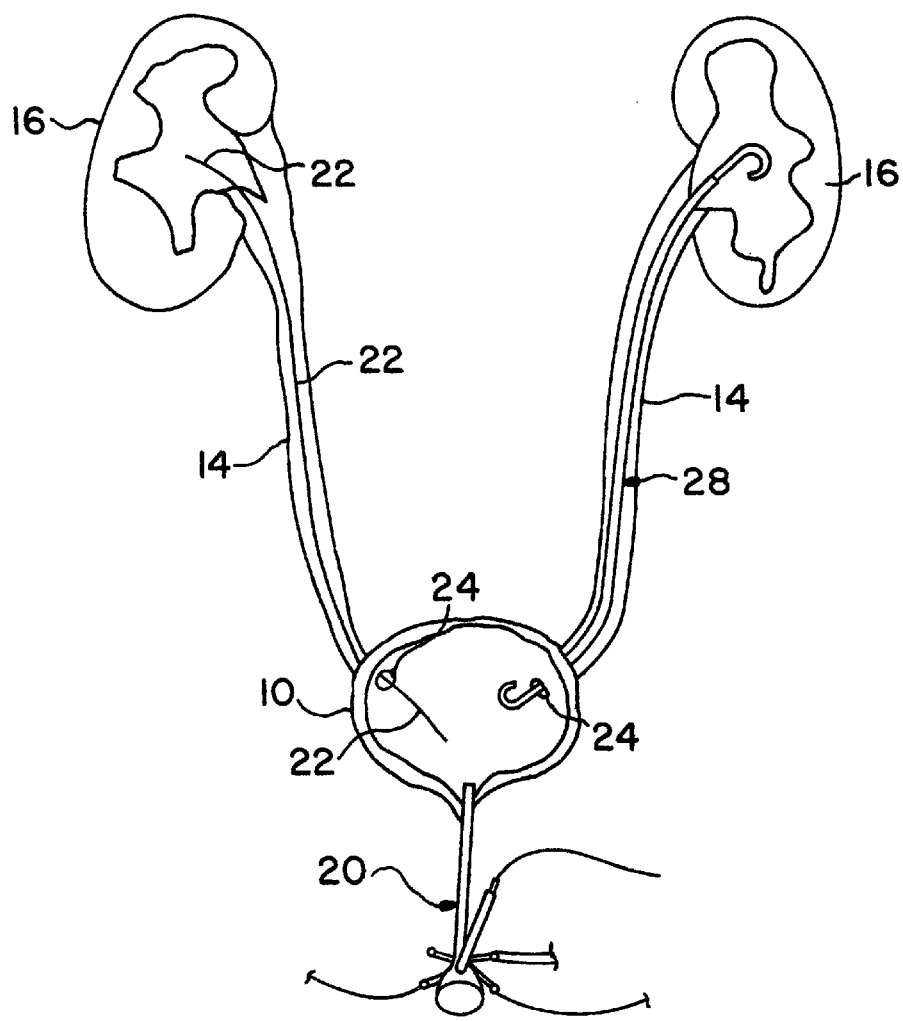
FIG. 3 is a simplified cross-sectional view of organs in the abdominal region of an individual, including the kidneys, ureters and urinary bladder.

Procedures utilizing a catheter device according to the invention will be described with reference to FIG. 3 which shows a urinary bladder 10 along with two ureters 14 and an associated pair of kidneys 16, each ureter 14 extending between a respective kidney 16 and the interior of bladder 10. Bladder 10, ureters 14 and the kidneys 16 are shown in cross section.

In the first step for inserting a device according to the invention, an instrument, such as a cystoscope 20, can be introduced via the urethra into bladder 10. Then, a guide wire 22 may be introduced, in a known manner, through cystoscope 20 and into an outlet orifice 24 of a respective ureter 14. Preferably, guide wire 22 is advanced until the distal end thereof is located within kidney 16.

Figure 4:
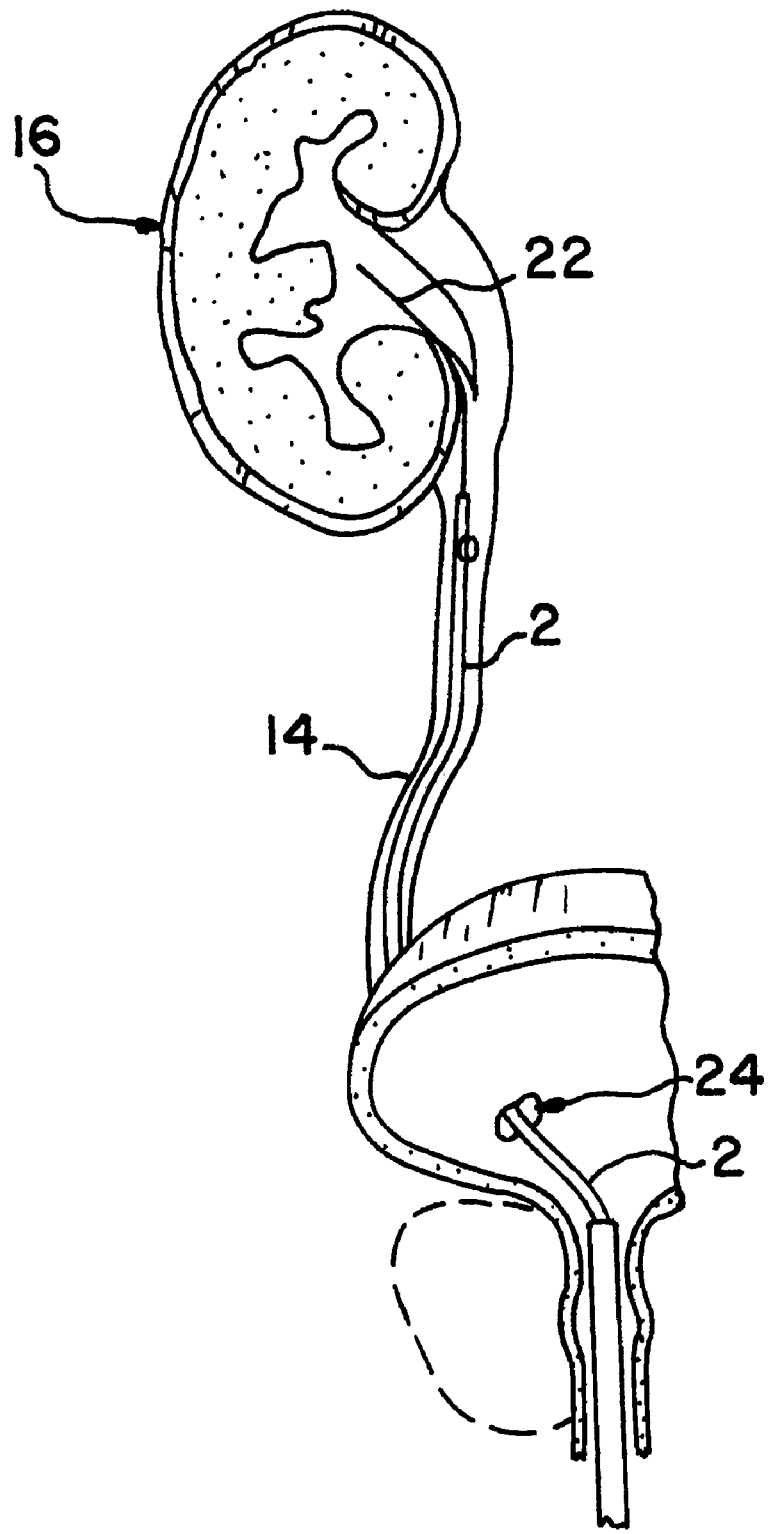
FIG. 4 is a pictorial view showing a portion of the organs shown in FIG. 3.

Then, referring to FIG. 4, a ureteral catheter device, such as shown in FIGS. 1 and 2, will be placed over guide wire 22, i.e. so that guide wire 22 extends through lumen 4. Body 2 will then be advanced, under guidance of guide wire 22, into the associated ureter 14, so that body 2 extends along any desired portion of the length of the associated ureter 14.

Of course, in accordance with the invention, a second guide wire can be introduced into the other ureter 14 and a second catheter device according to the invention can then be introduced into that ureter 14 by being guided along the second guide wire.

After a device according to the invention has been introduced into a ureter 14, guide wire 22 may be withdrawn, thereby giving lumen 4 a larger free cross-sectional area for drainage of urine. At the completion of the surgical procedure, it may be desired to insert a device, such as a double J stent 28. This may be effected by reinserting guide wire 22 via lumen 4 into a kidney 16, then withdrawing catheter 2 from the ureter 14 and bladder 10, and finally placing double-J stent 28 over guide wire 22 and sliding stent 28 along guide wire 22 to a desired final position, as shown at the right-hand side of FIG. 3. After such a stent has been inserted, guide wire 22 may be removed.

When a catheter device according to the invention is in place in a ureter 14, lumen 4 may also be employed for the injection of either radiographic dye or a colored dye, such as methalene blue, for the purpose of identifying any possible injury to the ureter by observation of any dye leaking from the ureter by radiographs or visually.

Because a device according to the invention employs a single fiber optic filament 6 for transmitting light to body 2 the cost of fabrication of such a device is less than that of known devices of this type.

Guide wire 22 is preferably of a hydrophilic material, which increases the ease of its insertion through any pathology. The distal end of guide wire 22 may have either a floppy tip or a J-tip which is maneuverable. Both of these types of tips facilitate insertion past any obstructive or tortuous pathology in the ureter. If there were a stenosis of the ureter, the guide wire could be used for guiding a dilator or a balloon which can be expanded to open the path defined by the ureter to permit introduction of the device according to the invention. Thus, the guide wire, once properly placed, facilitates introduction of a device according to the invention.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A ureteral illuminator device for visibly illuminating a ureter of a patient, comprising:

a tubular body having a substantial portion along a length thereof made of a visible-light transmitting material, said tubular body having a tubular peripheral wall and a distal end and a proximal end, said tubular body having an access lumen that extends between the distal and proximal ends and which has respective openings at both said distal and proximal ends, and said tubular body having a second lumen that extends substantially parallel to said access lumen, coupling means disposed at a proximal end of said illuminator for coupling visible-light into said illuminator, and light transmitting means consisting of a single fiber optic filament housed in said second lumen which receives said visible-light from said coupling means, said fiber optic filament being constructed so that said visible-light introduced at an input end of the filament is emitted laterally from an outer peripheral wall of the filament to visibly illuminate said illuminator along the length thereof through the ureter of the patient.

2. A method of installing an illuminator device in a ureter and a kidney of a patient, comprising the steps of:

a) providing a ureteral illuminator device, comprising:

a tubular body having a substantial portion along a length thereof made of a light transmitting material, said tubular body having a tubular peripheral wall and a distal end and a proximal end, said tubular body having a drainage lumen that extends between the distal and proximal ends and which has respective openings at both said distal and proximal ends, said tubular body having a second lumen that extends substantially parallel to said drainage lumen, and light transmitting means consisting of a single fiber optic filament to visibly illuminate said illuminator along a length thereof housed in said second lumen, said fiber optic filament being constructed so that light introduced at an input end of the filament is emitted laterally from an outer peripheral wall of the filament:

b) introducing a guide wire into the ureter via the patient's bladder;

c) placing the illuminator over the guide wire so that the guide wire is within the drainage lumen; and d) advancing the illuminator along the guide wire and into the ureter and kidney.

3. A method as defined in claim 2, further comprising the step of removing the guide wire from the illuminator after said step of advancing.

4. A method as defined in claim 3, further comprising the steps of: reintroducing the guide wire into the illuminator by passing the guide wire through the drainage lumen; withdrawing the illuminator from the ureter and the bladder while leaving the guide wire in the ureter; introducing a ureteral stent into the ureter while guiding the ureteral stent over the guide wire; and withdrawing the guide wire from the ureter while leaving the ureteral stent in place in the ureter.

5. The device of claim 1, wherein said tubular body has a diameter and length sufficient to fit into an ureter of a patient.

6. The device of claim 5, wherein said tubular body has a length of about 70 cm.

7. The device of claim 1, wherein said filament emits visible-light laterally along a substantial portion of the length of said filament.

8. The device of claim 7, wherein said filament emits visible-light around an entire periphery thereof.

9. The device of claim 8, wherein said filament is abraded to promote the emission of visible-light laterally.

10. The device of claim 1, wherein said fiber optic filament is fixedly located within said second lumen.

11. The device of claim 1, wherein said second lumen is sealed at the distal end of the tubular body.

12. The device of claim 1, wherein said illuminator has only two lumens, consisting of said access lumen and said second lumen, and wherein said second lumen is substantially smaller than said access lumen, has a substantially circular cross-section which corresponds to the diameter of said filament, and extends along a peripheral wall of said tubular body, and wherein said access lumen is substantially larger and has a generally circular cross-section with a concave region resulting from an inner wall around said second lumen.

13. The device of claim 1, wherein said second lumen is embedded in an outer wall of the tubular body that surrounds said access lumen, said second lumen being substantially smaller than said access lumen.

14. The device of claim 1, wherein said access lumen has a diameter sufficient to at least receive a guide wire having a diameter of about 0.038 inches.

15. The device of claim 1, wherein said openings at said distal and proximal ends are the only openings into said access lumen.

16. A method of illuminating an ureter of a patient, comprising the steps of:

providing an illuminator device, comprising: a tubular body, a drainage lumen that extends lengthwise through said tubular body, a second lumen that extends substantially parallel to the drainage lumen, and a single fiber optic filament housed in said second lumen;

introducing a guide wire into the ureter of the patient;

placing the tubular body over the guide wire with the guidewire within the drainage lumen;

advancing the tubular body along the guide wire and into the ureter of the patient; and introducing light into an input end of the single filament and emitting the light laterally from an outer peripheral wall of the filament with the light passing through a peripheral wall of the tubular body so as to illuminate said illuminator along a length thereof.

17. The method of claim 16, wherein said step of emitting the light laterally includes emitting the light so that a substantial portion of the length of the ureter is illuminated.

18. The device of claim 1, further including a guide wire for introducing the tubular body into the ureter of a patient, said guide wire fitting within said access lumen such that said tubular body can be moved along said guide wire.

19. The device of claim 18, wherein said guide wire has a diameter of at least about 0.038 inches.

20. The device of claim 1, further including a radiographic or colored dye introducible within said access lumen for identifying possible injury to the ureter by observation of said dye.

21. The device of claim 1, further including a radiographic or colored dye within said access lumen.

22. The device of claim 1, wherein said single fiber optic filament has a diameter of about 470 microns.

23. The device of claim 1, further including an outside visible light source, said coupling means coupling visible light from said outside visible light source into said single fiber optic filament.

24. The method of claim 2, further including the step of injecting a dye through the access lumen into the patient.

25. The method of claim 24, wherein said dye is a radiographic dye or a colored dye.

* * * * *